United States Patent [19]
Johnson

[11] Patent Number: 5,154,709
[45] Date of Patent: Oct. 13, 1992

[54] VACUUM HOOD ATTACHMENT FOR ELECTROSURGICAL INSTRUMENTS

[76] Inventor: Gerald W. Johnson, 17115 Red Oak, Ste. #211, Houston, Tex. 77090

[21] Appl. No.: 576,774

[22] Filed: Sep. 4, 1990

[51] Int. Cl.$^5$ .............................................. A61B 17/39
[52] U.S. Cl. ...................... 606/45; 606/49; 604/35
[58] Field of Search ............... 606/41, 42, 45, 49; 604/35

[56] References Cited

U.S. PATENT DOCUMENTS

| | | | |
|---|---|---|---|
| 2,102,270 | 12/1937 | Hyams | 606/49 |
| 4,562,838 | 1/1986 | Walker | 606/42 |
| 4,850,352 | 7/1989 | Johnson | 604/35 X |
| 4,943,290 | 7/1990 | Rexroth et al. | 606/45 |

FOREIGN PATENT DOCUMENTS 8706116 10/1987 World Int. Prop. O. ............ 604/35

*Primary Examiner*—Lee S. Cohen
*Attorney, Agent, or Firm*—Neal J. Mosely

[57] ABSTRACT

A vacuum hood attachment for electrosurgical instruments has a hollow tubular body open at each end and a side opening for connection to a source of vacuum. One of said end openings is to be fitted on the end of an electrosurgical instrument of a pencil- or pen-like or other hand held construction having an electrocauterizing or electrocutting blade secured therein. The other open end of said tubular body surrounds the blade along part of the length thereof. On connection to a source of vacuum during use, the hood attachment withdraws vapors and smoke from an operating site to keep the same clear for observation by the surgeon. This hood attachment fits a variety of shapes of electrosurgical instruments and may fit around the end of the instrument and/or into a recess in the end of the instrument depending on the construction of the instrument. The hood attachment may be secured by friction fit or clamped, wedged or cemented into place. Depending on the design of the electrosurgical instrument, the hood attachment may be cylindrical in shape or may be tapered or may have a portion to be fitted into a recess on the instrument. The hood attachment may be fixed in operation, and may have a portion constructed for extension and retraction.

9 Claims, 1 Drawing Sheet

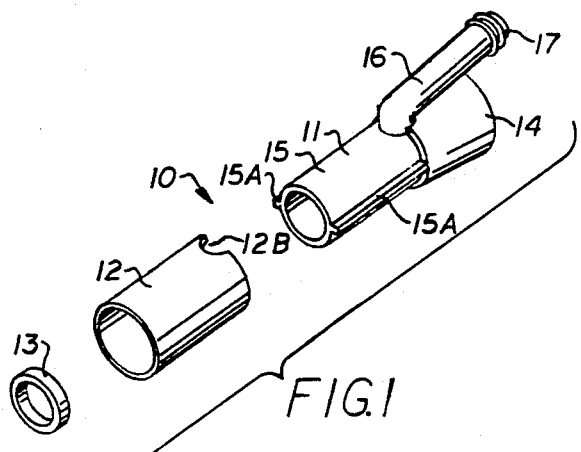
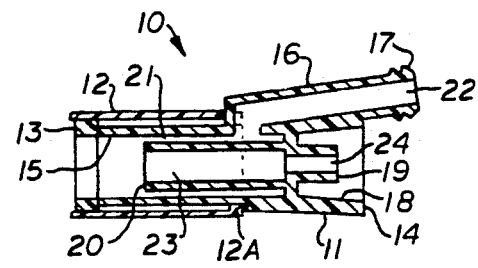
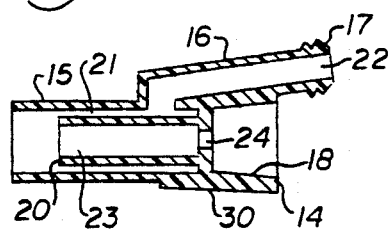
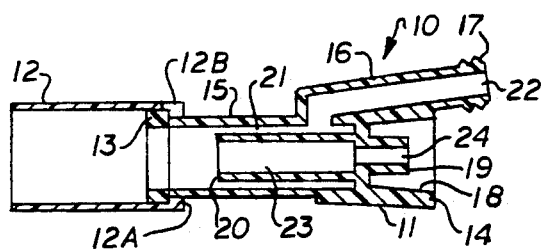
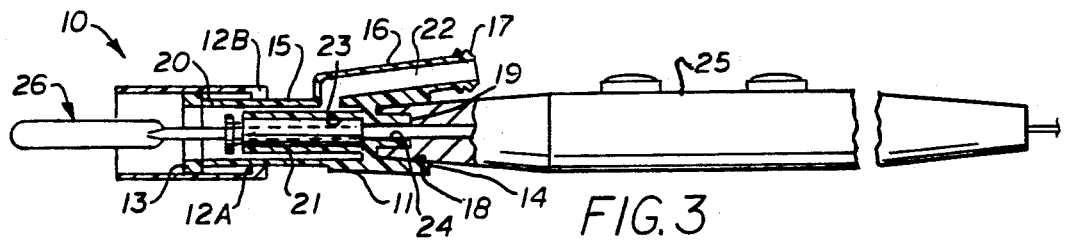
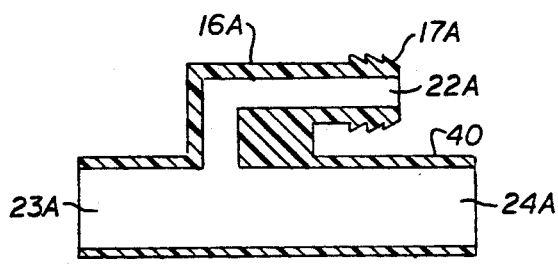
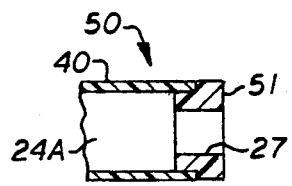

VACUUM HOOD ATTACHMENT FOR ELECTROSURGICAL INSTRUMENTS

BACKGROUND OF THE INVENTION

1. Field of the Invention

This invention relates to new and useful improvements in electrosurgical instruments, and more particularly to an attachment for an instrument having an electro-cauterizing and/or electro-cutting blade and provision for selective application of vacuum to the surgical site.

2. Brief Description of the Prior Art

Electrosurgical instruments having an electric cauterizing and/or electro-cutting blade and some means for aspirating blood and/or smoke from the surgical area have been disclosed in the literature for about 50 years.

Hyams U.S. Pat. No. 2,102,270 discloses an electrosurgical instrument for female sterilization procedures having an auxiliary tube surrounding the electric blade for introduction of a liquid for radiologically monitoring the operation.

Bierman U.S. Pat. No. 2,275,167 discloses an electrosurgical instrument for removal of tissue by electric current and having means for applying vacuum for drawing in and holding the tissue being cut.

August U.S. Pat. No. 2,808,833 discloses an electrocauterizing instrument with a tube for supplying an inert gas to blanket the surgical site.

Seiger U.S. Pat. NO. 2,888,928 discloses an electrocauterizing instrument with a tube for withdrawing blood and smoke from the surgical site by vacuum.

Morrison U.S. Pat. No. 3,828,780 discloses an electrocauterizing instrument with a tube for withdrawing blood and smoke from the surgical site by vacuum and having a side vent opening.

Roberts U.S. Pat. No. 3,906,955 discloses an electrocauterizing instrument with a tube for withdrawing blood and smoke from the surgical site by vacuum and constructed for easy replacement of the blade.

Durden U.S. Pat. No. 3,974,833 discloses an electrocauterizing instrument with a tube for withdrawing blood and smoke from the surgical site by vacuum and having a side vent opening arranged for selective opening and closing to control application of vacuum.

Walker U.S. Pat. No. 4,562,838 discloses an electrocauterizing instrument with a tube for supplying fluid to the surgical site for removing blood and smoke and having a light transmitting cable for illuminating the surgical site.

The present invention represents a new and useful improvement over these prior art references, and over my previous invention Johnson U.S. Pat. No. 4,719,914.

SUMMARY OF THE INVENTION

One of the objects of this invention is to provide a new and improved removable attachment for an electro-surgical and electro-cauterizing instrument having an evacuation system of more efficient design for removal of blood and smoke from the surgical site.

Another object of the invention is to provide a new and improved removable attachment for an electro-surgical and electro-cauterizing instrument having an evacuation system permitting selective application of vacuum during surgery.

Another object of the invention is to provide a new and improved removable attachment for an electro-surgical and electro-cauterizing instrument having an arrangement for enclosing the surgical site to force circulation of air through that region by application of vacuum.

Still another object of the invention is to provide a new and improved removable attachment for an electro-surgical and electro-cauterizing instrument having a hood or sleeve which is extensible to cause circulation of air through the surgical site and out through a vacuum connection by application of vacuum to the vacuum connection of the attachment of the instrument.

Other objects of the invention will become apparent from time to time throughout the specification and claims as hereinafter related.

The foregoing objects and other objects of the invention are accomplished by a vacuum hood attachment for electrosurgical instruments which has a hollow tubular body open at each end and a side opening for connection to a source of vacuum. One of said end openings is to be fitted on the end of an electrosurgical instrument of a pencil- or pen-like or other hand held construction having an electrocauterizing or electrocutting blade secured therein. The other open end of said tubular body surrounds the blade along part of the length thereof. On connection to a source of vacuum during use, the hood attachment withdraws vapors and smoke from an operating site to keep the same clear for observation by the surgeon. This hood attachment fits a variety of shapes of electrosurgical instruments and may fit around the end of the instrument and/or into a recess in the end of the instrument depending on the construction of the instrument. The hood attachment may be secured by friction fit or clamped, wedged or cemented into place. Depending on the design of the electrosurgical instrument, the hood attachment may be cylindrical in shape or may be tapered or may have a portion to be fitted into a recess on the instrument. The hood attachment may be fixed in operation, and may have a portion constructed for extension and retraction.

BRIEF DESCRIPTION OF THE DRAWINGS

FIG. 1 is an exploded isometric view of a preferred vacuum hood attachment for electrosurgical instruments in accordance with the present invention.

FIG. 2 is a cross-section view of the vacuum hood attachment for electrosurgical instruments of FIG. 2A represents the invention with the hood in the retracted position; 2B represents the invention with the hood in the extended position.

FIG. 3 is a partially cross-section, and partially side elevation view of a vacuum hood attachment, shown attached to an electrosurgical instrument.

FIG. 4 is a cross-section view of the vacuum hood attachment for electrosurgical instruments of FIG. 1, shown without the hood and hood stop ring.

FIG. 5 is a cross-section view of an alternate embodiment of a vacuum hood attachment for electrosurgical instruments.

FIG. 6 is a cross-section cut-away view of an adapter ring for the alternate embodiment of a vacuum hood attachment of FIG. 5.

DESCRIPTION OF THE PREFERRED EMBODIMENT

Referring to the drawings by numerals of reference, there is shown in FIGS. 1, 2A, and 2B, a preferred vacuum hood attachment 10 for installation on electrosurgical instruments. FIG. 1 is an exploded view showing the components in an unassembled condition for ease of understanding. The vacuum hood attachment 10 comprises a main body 11, a retractable hood or sleeve 12 for slidably mounting thereon and a stop ring 13 for mounting at the forward end of main body 11 to retain sleeve 12 thereon.

As seen in FIG. 1, the exterior surface of the tubular front portion 15 of main body 11 may also have circumferentially spaced longitudinal raised ribs 15A, and the tubular sleeve 12 has slots (not shown) in its reduced diameter portion which are slidably engaged on the ribs 15A. This arrangement prevents relative rotation between sleeve 12 and tubular front portion 15 of main body 11 and maintains the arcuate cut-out 12B aligned with the upstanding portion of the tubular hose connection portion or vacuum outlet 16.

In FIGS. 2A and 2B, the vacuum hood attachment 10 is shown in an assembled condition with sleeve 12 in a retracted position in FIG. 2A and in an extended position in FIG. 2B. The main body 11 is a generally tubular member having an outwardly tapered rear portion 14 and a straight tubular front portion 15. A tubular hose connection portion or vacuum outlet 16 extends outwardly and rearwardly from the main body 11 toward its rear portion 14 and its extended end 17 is configured for receiving and frictionally engaging the interior of a hose or length of tubing (not shown) which is connected to a vacuum pump or other source of vacuum (not shown).

The interior of the rear portion 14 of the main body 11 has a tapered or conical recess 18 to receive and frictionally engage the tapered nose portion of an electrosurgical instrument 25. A small tubular extension 19 coaxial with the recess 18 extends rearwardly a short distance inside the recess to be received within a cavity in the front end or tip of the electrosurgical instrument 25. Another tubular extension 20 coaxial with tubular front portion 15 extends forwardly a distance therein and terminates a distance inwardly from the front end thereof. The tubular extension 20 is spaced inwardly from the side wall of the tubular portion 15 to form an annulus 21 therebetween communicating with the interior 22 of the tubular hose connection portion 16.

A central bore 23 extending through the tubular extension 20 terminates in a smaller bore 24 extending through the tubular extension 19. The smaller bore 24 receives the shaft of a cutting and cauterizing blade 26 installed in the electrosurgical instrument 25 and the bore 23 receives conventional locking means for supporting and securing the forward end of the cutting and cauterizing blade against rotation.

The retractable hood or sleeve 12 is hollow and has reduced diameter portion 12A at its rearward end which is slidably received on the straight tubular portion 15 of the main body 11. The reduced diameter portion 12A defines an annular stop shoulder. The side wall of the sleeve 12 preferably has an arcuate recess 12B fitting the upstanding portion of the hose connection portion or vacuum outlet 16 when the sleeve is in the rearmost retracted position.

The stop ring 13 secured on the front end of the tubular portion 15 has an exterior diameter slightly larger than the exterior of the tubular portion 15 to form an annular stop shoulder at the front end thereof. Thus, as seen in FIG. 2A, the sleeve 12 is slidable longitudinally on the straight tubular front portion 15 of the main body 11. In its forwardmost extended position, the stop shoulder 12A of the sleeve 12 will engage the stop ring 13 at the front end of the tubular front portion 15 to prevent the sleeve from sliding completely off.

Referring now to FIG. 3, the vacuum hood attachment 10 of FIG. 1 is shown connected to an electrosurgical instrument 25. A central bore 23 through the tubular extension 20 terminates in a smaller bore 24 extending through the tubular extension 19. The smaller bore 24 receives the shaft of a cutting and cauterizing blade 26 installed in the electrosurgical instrument 25 and the bore 23 receives conventional locking means for supporting and securing the forward end of the cutting and cauterizing blade 26 against rotation.

A cutting and cauterizing blade 26 is supported in the end of nose portion 13 and extends inside the vacuum hood attachment 10 where it is connected to an electric power source (not shown). While FIG. 3 illustrates a preferred embodiment of the vacuum hood attachment 10 for one particular electrosurgical instrument, it should be understood that various modifications may be incorporated to provide vacuum hood attachments to fit various other electrosurgical instruments.

One example of the various applications of the vacuum hood attachment is shown in FIG. 4, which shows a modified main body 30, in which the small tubular extension 19 within the recess 18 has been eliminated and the main body is adapted to be frictionally engaged by the recess 18 onto an electrosurgical instrument. The modified main body 30 may or may not have the sliding sleeve 12 and stop ring 13. In other words, the main body 30 may be a unitary member with a fixed tubular front portion 15.

The main body 30 is a generally tubular member having an outwardly tapered rear portion 14 and a straight tubular front portion 15. A tubular hose connection portion 16 extends outwardly and rearwardly from the main body 30 toward its rear portion 14 and its extended end 17 is configured for receiving and frictionally engaging the interior of a hose or length of tubing (not shown) which is connected to a vacuum pump or other source of vacuum (not shown).

The interior of the rear portion 14 of the main body 30 has a tapered or conical recess 18 to receive and frictionally engage the tapered nose portion of an electrosurgical instrument. Another tubular extension 20 coaxial with the tubular front portion 15 extends forwardly a distance therein and terminates a distance inwardly from the front end thereof. The tubular extension 20 is spaced inwardly from the side wall of the tubular portion 15 to form an annulus 21 therebetween which communicates with the interior 22 of the tubular hose connection portion 16.

A central bore 23 extends through the tubular extension 20 and terminates in a smaller bore 24. The smaller bore 24 receives the shaft of a cutting and cauterizing blade installed in the electrosurgical instrument and the bore 23 receives conventional locking means for supporting and securing the forward end of the cutting and cauterizing blade against rotation.

FIG. 5 shows another modification of the vacuum hood attachment 40 wherein there is no sliding sleeve or stop ring, and the rearward portion is not tapered but rather has a straight bore for fitting another type or model of electrosurgical instrument.

The main body 40 is a generally tubular member. A tubular hose connection portion 16A extends outwardly and rearwardly from the main body 40 toward its rear portion and its extended end 17A is configured for receiving and frictionally engaging the interior of a hose or length of tubing (not shown) which is connected to a vacuum pump or other source of vacuum (not shown).

In this configuration, the front bore 23A and rear bore 24A have the same diameter. The passageway formed between the front bore 23A and rear bore 24A communicates with the interior 22A of the tubular hose connection portion 16A. As shown in FIG. 5, the extended end 17A is configured such that it is parallel to the main body 40

FIG. 6 shows still another modification of the vacuum hood attachment 50 wherein there is no sliding sleeve or stop ring and the rearward portion is not tapered but rather has a straight bore 24A. In this modification, a unitary main body 40 allows connection to a vacuum source (as in FIG. 5), and its rearward end is adapted to receive one or more adapter plugs 51 configured to fit onto various electrosurgical instruments.

In this configuration, the rear bore 27 receives the shaft of a cutting and cauterizing blade installed in the electrosurgical instrument, and the front bore receives conventional locking means for supporting and securing the forward end of the cutting and cauterizing blade against rotation. The front end or tip of the electrosurgical instrument is frictionally engaged to the adapter unit 51.

OPERATION

While the operation of the vacuum hood attachment for electrosurgical instruments should be obvious from the preceding description, it will be stated in detail for clarity.

The vacuum hood attachment for electrosurgical instruments 10 is used in surgical operations in a manner similar to that of the prior art instruments. The vacuum connection 11 is connected to a source of vacuum (not shown) by tubing. The blade 17 is connected to a power source (not shown).

When the surgical procedure is being performed with blade 17 extending into the tissue being cut, the hood 14 is used in a retracted position. If the blade 17 is used for cauterizing, there is a substantial evolution of smoke and gases, which is withdrawn through the attachment 10 by the vacuum applied through the tubing.

When the blade 17 is used for cutting or cauterizing in the open, the sleeve 12 is moved to its most extended position adjacent to the cutting end of blade 17 as shown in FIG. 2B. In this position, the sleeve 12 is positioned substantially at the surgical site, and defines an opening extending back to the vacuum connection 11 of the attachment, which provides for efficient removal of smoke and gases.

In the various embodiments of the invention, the vacuum hood attachment 10 for electrosurgical instruments may be secured by press fit or interference fit, or by adhesive or heat sealing, or by screw connection or bayonet connection where the electrosurgical instrument has a complementary connecting portion. The press fit or interference fit may be on the exterior of the electrosurgical instrument or in an interior cavity therein.

While this invention has been described fully and completely with special emphasis on the preferred embodiment, it should be understood that within the scope of the appended claims, the invention may be practiced otherwise than as specifically described herein.

I claim:

1. A vacuum hood attachment for a hand held electro-surgical instrument comprising a tubular member with a tapered hollow nose portion, a cutting element comprising an electrocauterizing blade secured in and having one end extending outward from said nose portion, and the other end of said blade positioned inside said instrument tubular member, and electric heating means for said electrocauterizing blade including an electric lead extending through said tubular member for connection to a power source, said hood attachment comprising a first hollow tubular member having openings at opposite ends, one of said openings being of a size and shape tapered for removably fitting the nose portion of aid electrosurgical instrument, the second of said openings being spaced to fit over at least a part of the length of said blade, said first tubular member having a side opening comprising a second hollow tubular member integral with and forming an outlet from said first tubular member, and adapted to receive tubing for connection to a source of vacuum, and a hollow tubular sleeve slidably supported on said first hollow tubular member and movable to extend and retract an open end relative to said cutting element.

2. A vacuum hold attachment for a hand-held electrosurgical instrument according to claim 1 in which said second hollow tubular member communicates with said hollow tubular sleeve for selective application of vacuum to the surgical site.

3. A vacuum hood attachment for a hand-held electrosurgical instrument according to claim 2 in which said hollow tubular sleeve and said first hollow tubular member include stop means preventing removal of said sleeve on fully extended movement.

4. A vacuum hood attachment for a hand-held electrosurgical instrument according to claim 2 in which said hollow tubular sleeve has an inwardly directed flange and said first hollow tubular member has an outwardly directed flange cooperable to provide stop means preventing removal of said sleeve on fully extended movement.

5. The combination of a vacuum hood attachment with a hand-held electrosurgical instrument in which said electrosurgical instrument comprises a tubular member with a tapered hollow nose portion, an electrocutting and electrocauterizing blade secured in and having one end extending outward from said nose portion, the other end of said blade being positioned inside said instrument tubular member, electric heating means for said electrocauterizing blade including an electric lead extending through said tubular member for connection to a power source, and said vacuum hood attachment comprising:

a first hollow tubular member having openings at opposite ends, one of said tubular member openings having a tapered surface removably fitting said nose portion of said electrosurgical instrument, providing a tight connection therebetween as assembled, another tubular member opening being spaced to fit over at least a part of the length of said blade, said first hollow tubular member having a side opening for connection to a source of vacuum, and a hollow tubular sleeve with an open end slidably supported on said first hollow tubular member and movable to extend and retract said open end relative to said blade.

6. The combination of a vacuum hood attachment with a hand-held electrosurgical instrument in which said electrosurgical instrument comprises a tubular member with a tapered hollow nose portion, a cutting element comprising an electrocutting and electrocauterizing blade secured in and having one end extending outward from said nose portion, the other end of said blade being positioned inside said instrument tubular member, electric heating means for said electrocauterizing blade including an electric lead extending through said tubular member for connection to a power source, and said vacuum hood attachment comprising:

a first hollow tubular member having openings at opposite ends, one of said tubular member openings having a tapered surface removably fitting said nose portion of said electrosurgical instrument, providing a tight connection therebetween as assembled, another tubular member opening being spaced to fit over at least a part of the length of said blade, said first hollow tubular member having a side opening comprising a second hollow tubular member forming an outlet from said first tubular member, and adapted to receive tubing for connection to vacuum, and a hollow tubular sleeve slidably supported on said first hollow tubular member and movable to extend and retract an open end relative to said cutting element.

7. The combination of a vacuum hood attachment with a hand-held electrosurgical instrument according to claim 6 in which said second hollow tubular member communicates with said hollow tubular sleeve for selective application of vacuum to the surgical site.

8. The combination of a vacuum hood attachment with a hand-held electrosurgical instrument according to claim 7 in which said hollow tubular sleeve and said first hollow tubular member include stop means preventing removal of said sleeve on fully extended movement.

9. The combination of a vacuum hood attachment with a hand-held electrosurgical instrument according to claim 7 in which said hollow tubular sleeve has an inwardly directed flange and said first hollow tubular member has an outwardly directed flange cooperable to provide stop means preventing removal of said sleeve on fully extended movement.

* * * * *